United States Patent [19]

Pinol et al.

[11] Patent Number: 5,073,646
[45] Date of Patent: Dec. 17, 1991

[54] SUBSTITUTED 1-DIPHENYLMETHYL AZETIDINES

[75] Inventors: Augusto C. Pinol; Jordi F. Constansa; Juan P. Corominas, all of Barcelona, Spain

[73] Assignee: Laboratorios Del Dr. Esteve, S.A., Barcelona, Spain

[21] Appl. No.: 541,056

[22] Filed: Jun. 20, 1990

[30] Foreign Application Priority Data

Jun. 29, 1989 [FR] France ................ 89 08696

[51] Int. Cl.$^5$ .......................................... C07D 205/04
[52] U.S. Cl. ....................................................... 548/953
[58] Field of Search ......................................... 548/953

[56] References Cited

U.S. PATENT DOCUMENTS 3,929,755 12/1975 Suzaki et al. ................ 548/953
4,822,895 4/1989 Nisato et al. ................ 548/953

FOREIGN PATENT DOCUMENTS 0153163 8/1985 European Pat. Off. .
0155870 9/1985 European Pat. Off. .
3627246 2/1988 Fed. Rep. of Germany .
2150816 4/1973 France .

OTHER PUBLICATIONS

CA 82(5): 31187p (1973).
CA 78: 135964y (1975).

Primary Examiner—Mukund J. Shah
Assistant Examiner—Jyothsna Venkat
Attorney, Agent, or Firm—Dressler, Goldsmith, Shore, Sutker & Milnamow, Ltd.

[57] ABSTRACT

New azetidines, characterized in that they correspond to the general formula (I)

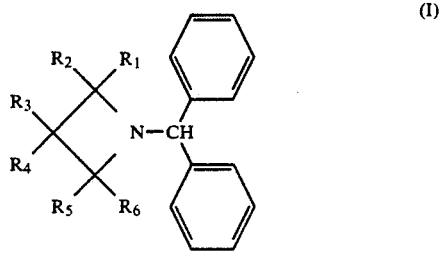

in which $R_3$ represents an amino radical, an alkylamino radical, a dialkylamino radical, a cycloalkylamino radical, an acylamino radical, an alkylacylamino radical, an aminomethyl radical, an alkylaminomethyl radical, an acylaminomethyl radical or an alkylacylaminomethyl radical, in which radicals each acyl fragment may be substituted with one or more halogen, especially fluorine, atoms; and $R_1$, $R_2$, $R_4$, $R_5$ and $R_6$ represent a hydrogen atom or a lower alkyl radical, with the proviso that at least one of them represents a lower alkyl radical, and also their salts.

3 Claims, No Drawings

SUBSTITUTED 1-DIPHENYLMETHYL AZETIDINES

The present invention relates to new chemical intermediates corresponding to the general formula I, to a process for preparing these and also to their application for the preparation of biologically active substances.

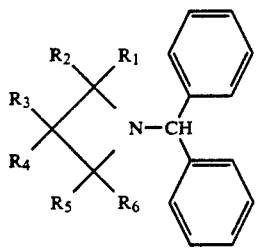
(I)

The compounds of general formula II

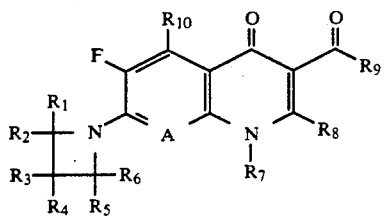
(II)

have been described in European Patent EP 88/403352.3 and French Patents FR 89/03,459 and FR 89/05,129. Some of these compounds are in the process of development on account of their excellent antimicrobial activities.

It is important to obtain intermediates which are simple and efficient and synthetic routes for the compounds of general formula (II) which contain the 1-azetidinyl group (III)

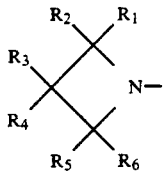
(III)

A few derivatives of general formula (I) in which $R_3$ represents an amino, alkylamino, dialkylamino, aminomethyl or alkylaminomethyl radical are known in the scientific literature, but there is no example of compounds of general formula (I) in which $R_3$ has the meaning stated and at least one of the other substituents simultaneously represents a lower alkyl radical. The amino-substituted compounds of general formula (I) described hitherto in the scientific literature are to be found in Chemical Abstracts, 108(13):1120223q, 105(15):133737d, 104(23):207074g, 104(5):34013n, 101(9):72740t, 78(21):135969d, 83(1):9760u, 90(11):80717k and 78(3):15930n.

We have now discovered, according to the present invention, that the compounds of general formula (I) in which $R_3$ represents an amino radical, an alkylamino radical, a dialkylamino radical, a cycloalkylamino radical, an acylamino radical, an alkylacylamino radical, an aminomethyl radical, an alkylaminomethyl radical, an acylaminomethyl radical or an alkylacylaminomethyl radical, in which radicals each acyl fragment may be substituted with one or more halogen, especially fluorine, atoms; and $R_1$, $R_2$, $R_4$, $R_5$ and $R_6$ represent a hydrogen atom or a lower alkyl radical, with the proviso that at least one of them represents a lower alkyl radical, are new compounds which are useful as intermediates for the preparation of therapeutically active compounds such as quinolones, naphthyridines, pyridobenzoxazines, thiazetoquinolones, benzoquinolizines, benzothiazoloquinolones, pyridobenzothiazines, benzoxazoloquinolones, epoxymethanothiazoloquinolones and isothiazoloquinolines of general formula (II).

The new azetidines of general formula (I) can have, depending on the number, nature and relative position of the substituents, up to three chiral centres, each of them with an "R" or "S" configuration.

The compounds of general formula (I) in which $R_1$, $R_2$, $R_3$, $R_4$, $R_5$ and $R_6$ have the meaning stated above are products obtained by substitution of $R_3$, when it represents a good "leaving group", by an appropriate nucleophile. This substitution is very advantageous as regards the yields, on account of the presence of the benzhydryl group as a group protecting the azetidine at the 1-position. In addition, the benzhydryl group is also very advantageous as regards the yields for the deprotection which leads to the azetidines of general formula (IV), which are necessary for preparing the compounds of general formula (II) as has been described in U.S. Pat. Nos. EP 324,298, EP 90/400684.8 and EP 90/401036.0.

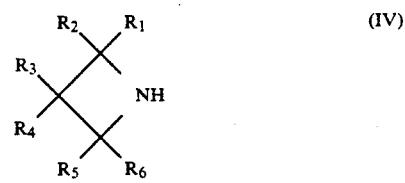
(IV)

Another additional advantage of the use of the benzhydryl radical as a protective group in the compounds of general formula (I) occurs in the cases where there are chiral carbons since, when the substitution reactions mentioned above are performed, a retention of configuration is observed, thereby avoiding the formation of mixtures of stereoisomers. Furthermore, the compounds of general formula (I) are very suitable for performing the resolution of racemic mixtures by means of the use of enzymes or of enantiomerically pure organic acids.

The present invention also relates to the preparation of the compounds of general formula (I). The new derivatives which are the subject of the invention may be prepared according to Scheme 1, which leads by all the pathways to the intermediates of general formula (XI) which, by successive reactions, give rise to compounds of general formula (I). In the compounds (V) to (XIII) of Scheme 1, the radicals $R_1$, $R_2$, $R_4$, $R_5$ and $R_6$ have the meaning stated above, X represents a chlorine atom, a bromine atom, a hydroxyl radical, an acetyloxy radical, a methylsulphonyloxy radical, a p-toluenesulphonyloxy radical, a p-nitrobenzoyloxy radical, a 2-naphthalenesulphonyloxy radical, a tert-butyldiphenylsilyloxy radical or a tert-butyldimethylsilyloxy radical, Y represents a chlorine atom or a bromine atom and Z represents a methylsulphonyloxy radical, a p-toluenesulphonyloxy radical or a cyano radical.

According to one of its aspects, the subject of the present invention is the preparation of the compounds of general formula (I) according to Scheme 1:

method described previously (A. H. Yavronian, R. A. Sanchez, J. K. Pollard and E. K. Metzner, *Synthesis*, 1981, 791). In the case where an asymmetric epoxydation is performed, the preferred reagent is tert-butyl hydroperoxide in the presence of titanium isopropoxide

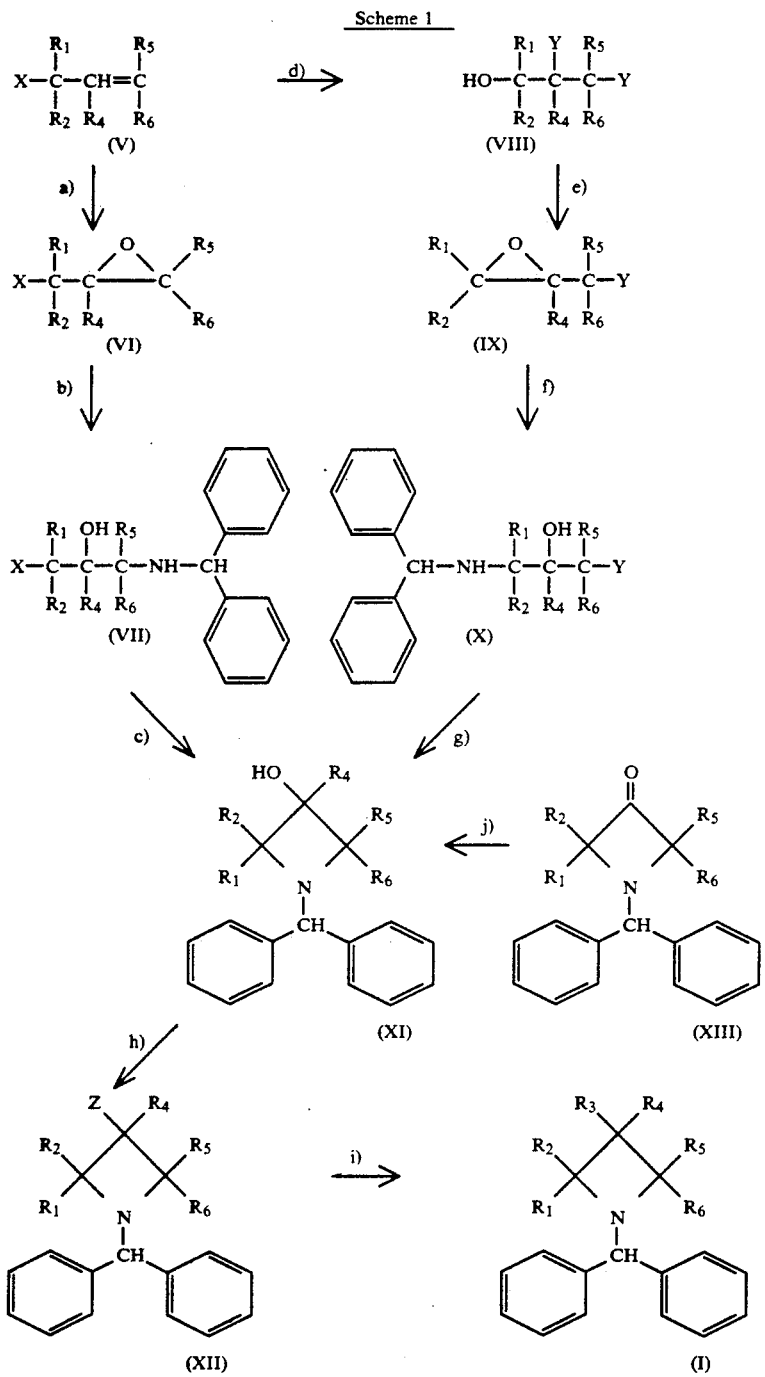

Synthesis of the epoxides (VI) or (IX)

a) By reaction of a compound of general formula (V) with an oxidizing agent such as peracetic acid, m-chloroperbenzoic acid, N-bromosuccinimide or tert-butyl hydroperoxide, the epoxide of general formula (VI) is obtained.

When N-bromosuccinimide is used as an oxidizing agent, the reaction is performed in water according to a and diethyl tartrate, and for the kinetic resolution isopropyl tartrate, dicyclohexyl tartrate or dicyclododecyl tartrate may be used, as described previously (Y. Gao, M. Hanson, J. M. Klunder, S. Y. Ko, H. Masamune and K. B. Sharpless, *J. Am. Chem. Soc.*, 1987, 109, 5765).

d,e) By addition of bromine or chlorine to the compounds of general formula (V) in which X represents OH, and subsequent treatment with a base such as potassium hydroxide, the epoxides of general formula (IX) are obtained, as described previously for a few compounds (C. F. Hiskey, H. L. Slates and N. L. Wendler, *J. Org. Chem.*, 1956, 21, 429; R. H. Higgins and N. H. Cromwell, *J. Heterocyclic Chem.* 1971, 1059). The reaction is performed without carrying out the isolation of the intermediate compounds of general formula (VIII).

Synthesis of the azetidinols (XI)

b,c) or f,g) The compounds of general formula (XI) are synthesized from the compounds of general formula (VI) or (IX) by reaction with diphenylmethylamine without isolating the intermediate products (VII) or (X), respectively.

The reaction is performed in a polar solvent such as methanol or ethanol, for a time between two days and ten days. The appropriate temperature for performing the opening of the epoxide varies between 0° C. and 30° C. and the appropriate temperature for the cyclization varies between 20° C. and the boiling point of the solvent used.

j) The ketones of general formula (XIII), by treatment with alkyllithium ($R_4Li$) or alkylmagnesium halides ($R_4MgX$), give rise to the corresponding 3-alkyl-3-azetidinols of general formula (XI), as described previously (S. S. Chatterjee and A. Shoeb, *Synthesis*, 1973, 153).

Synthesis of the azetidines of general formula (XII)

h1) The compounds of general formula (XII) in which Z represents a methylsulphonyloxy radical or a p-toluenesulphonyloxy radical are synthesized by reaction of the compounds of general formula (XI) with methanesulphonyl chloride or p-toluenesulphonyl chloride, respectively. The reaction is preferably performed in chlorinated solvents such as methylene chloride or chloroform, tertiary amines such as pyridine or triethylamine, or alternatively mixtures of these solvents. The reaction is performed at temperatures of between −30° C. and 40° C. for times between 1 hour and 24 hours.

h2) The compounds of general formula (XII) in which Z represents a cyano radical are synthesized by reaction of the compounds of general formula (XII) in which Z represents a methylsulphonyloxy radical or a p-toluenesulphonyloxy radical with sodium cyanide. The reaction is performed using a suitable solvent such as dimethylformamide or dimethyl sulphoxide. The reactants are kept stirring for a time between 3 and 8 hours, at a temperature which varies between 50° C. and 100° C.

Synthesis of the azetidines of general formula (I)

i1) The compounds of general formula (I) in which $R_3$ represents an amino radical, an alkylamino radical, a dialkylamino radical or a cycloalkylamino radical are obtained by reaction of a compound of general formula (XII) in which Z represents a methylsulphonyloxy or p-toluenesulphonyloxy radical with ammonia solution, an alkylamine, a dialkylamine or a cycloalkylamine, respectively. The reaction is performed in a suitable solvent, at temperatures of between 40° C. and 120° C., for times between 1 hour and 48 hours, either at atmospheric pressure or in a closed vessel. The suitable solvents are water, aprotic and dipolar solvents such as dimethylformamide or dimethyl sulphoxide, alcohols such as ethanol or isopropanol, ethers such as tetrahydrofuran or dioxane, or alternatively a mixture of two of the solvents mentioned.

i2) The compounds of general formula (I) in which $R_3$ represents an aminomethyl radical are obtained by reduction of a compound of general formula (XII) in which Z represents a cyano radical. This reduction is preferably performed with the aid of a metal hydride such as lithium aluminium hydride in an ether such as diethyl ether or tetrahydrofuran. The temperature is maintained at between 25° and 40° C. during the addition of the nitrile, and the reactants are subsequently stirred for a time between 12 and 24 hours at room temperature (25° C).

i3) The compounds of general formula (I) in which $R_3$ represents an acylamino radical, an alkylacylamino radical or an acylaminomethyl radical are obtained by reaction of the compounds of general formula (I) in which $R_3$ represents an amino radical, an alkylamino radical or an aminomethyl radical, respectively, with a carboxylic acid chloride or with a carboxylic acid anhydride. This reaction is preferably performed in an aromatic hydrocarbon such as benzene or toluene, a chlorinated compound such as methylene chloride or chloroform, or alternatively mixtures of these solvents. In addition, the presence of an inorganic base such as sodium carbonate or an organic base such as pyridine or triethylamine is desirable. The appropriate temperatures vary between 0° C. and 30° C., for a time between 1 hour and 4 hours.

i4) The compounds of general formula (I) in which $R_3$ represents an alkylacylaminomethyl radical are obtained by alkylation of the compounds of general formula (I) in which $R_3$ represents an acylaminomethyl radical, using an alkyl halide as an alkylating agent. The reaction is performed according to a process similar to that described for the alkylation of other trifluoroacetylamides P. A. Harland, P. Hodge, W. Maughan and E. Wildsmith, *Synthesis*, 1984, 941).

i5) The compounds of general formula (I) in which $R_3$ represents an alkylaminomethyl radical are obtained by hydrolysis of the compounds of general formula (I) in which $R_3$ represents an alkylacylaminomethyl radical. This hydrolysis is performed in a basic medium, preferably with the aid of an alkali metal base such as sodium hydroxide or potassium hydroxide, at temperatures of between 40° C. and 100° C.

The compounds of general formula (I) which are the subject of the present invention have the advantage of being very stable and readily convertible to the azetidines of general formula (IV), which are the compounds necessary for synthesizing compounds with antimicrobial activity of general formula (II).

The reaction which enables the compounds of general formula (I) to be converted to the compounds of general formula (IV) consists of a hydrogenolysis using a palladium catalyst, preferably palladium hydroxide. The reaction is performed in an alcohol such as methanol or ethanol at a hydrogen pressure of between 1.1 atm. and 20 atm., and the appropriate temperatures vary between 20° C. and 70° C.

In the examples which follow, the preparation of the new derivatives according to the invention is described. The examples below, given simply by way of illustration, are not, however, to limit the scope of the invention in any way.

EXAMPLE 1

Preparation of 3-amino-1-diphenylmethyl-3-methylazetidine a) 1-Chloro-2,3-epoxy-2-methylpropane. 534 g (3.0 mol) of N-bromosuccinimide are added to a suspension of 294 ml (3.0 mol) of methallyl chloride in 1.5 l of water with vigorous stirring and at room temperature. The mixture is stirred for 16 hours and cooled to 10° C., and 50% strength aqueous sodium hydroxide (3 mol) is added at a rate such that the temperature is maintained at approximately 25° C. The mixture is kept stirring for 2 hours, the lower organic phase is separated, dried with magnesium sulphate (20 g) and evaporated, and 266 g (84%) of crude product are obtained. Extraction of the aqueous phase with chloroform (250 ml) gives a further 50 g (12%). The product may be used directly for the next stage, but it is preferable to distil in order to remove the last traces of succinimide (boiling point 65° C./40 torr).

Spectroscopic data:

$^1$H NMR, , δ, (CDCl$_3$): 1.47 (s,3H); 2.72 (d,J=5.0 Hz, 1H); 2.79 (d,J=5.0 Hz, 1H); 3.52 (s,2H).

b,c) 1-Diphenylmethyl-3-hydroxy-3-methylazetidine. 12.5 g (117.3 mmol) of 1-chloro-2,3-epoxy-2-methylpropane are added to a solution of 21.5 g (117.3 mmol) of diphenylmethylamine dissolved in 50 ml of methanol, and the mixture is left for 3 days at room temperature and subsequently for 3 days under reflux. The methanol is evaporated off under reduced pressure, the resulting solid is washed with acetone and filtered off, and 28.8 g (85%) of 1-diphenylmethyl-3-hydroxy-3-methylazetidine hydrochloride, melting point 187°-197° C., are obtained.

Spectroscopic data: $^1$H NMR, δ, (DMSO-d:): 1.49 (m,3H); 3.95 (m,4H); 6.06 (m,2H); 7.1-7.9 (m,10H); 12.2-12.7 (b,1H)

IR (KBr): 3322, 2587, 1455, 1242, 704 cm$^{-1}$

The base is liberated by extraction with chloroform in 10% strength sodium hydroxide solution and 1-diphenylmethyl-3-hydroxy-3-methylazetidine is obtained in a 98% yield.

Spectroscopic data:

$^1$H NMR, δ, (CDCl$_3$) 1.66 (s,3H); 3.10 (d,J=8 Hz, 2H); 3.33 (d,J=8 Hz, 2H); 4.50 (s,1H); 7.1-7.7 (m,10H).

j) 1-Diphenylmethyl-3-hydroxy-3-methylazetidine. 1.41 g of methyllithium (64 mmol) in 140 ml of anhydrous ether are added dropwise to a solution, cooled to 0° C., of 3.05 g (12.8 mmol) of 1-diphenylmethyl-3-azetidinone in 61 ml of anhydrous ether, and the reaction is maintained for 2 hours at 0° C. Water is then added dropwise. The organic phase is washed with water, dried with anhydrous sodium sulphate and evaporated to dryness. The resulting solid is dissolved in methanol, methanol saturated with hydrochloric acid is added and the mixture is evaporated to dryness. The resulting solid is washed with acetone and filtered off, and 3.12 g (84%) of 1-diphenylmethyl-3-hydroxy-3-methylazetidine hydrochloride, melting point 187°-197° C., are obtained.

h) 1-Diphenylmethyl-3-methyl-3-methylsulfonyloxyazetidine. 5.3 g (46.8 mmol) of methanesulphonyl chloride are added dropwise to a solution, cooled to −20° C., of 7.9 g (31.2 mmol) of 1-diphenylmethyl-3-hydroxy-3-methylazetidine in 70 ml of pyridine. The temperature is maintained at −20° C. for one hour and the mixture is left at 4° C. for 12 hours. It is then poured onto a water/ice mixture, and the precipitate formed is filtered off and washed with water. The solid is dissolved in methylene chloride, the remaining water is separated after settling has taken place, the organic phase is dried with anhydrous sodium sulphate and the solvent is evaporated off under reduced pressure. The solid obtained is recrystallized with a methylene chloride/heptane mixture and 7.2 g (70%) of 1-diphenylmethyl-3-methyl-3-methylsulphonyloxyazetidine, melting point 113°-115° C., are obtained.

Spectroscopic data:

$^1$H NMR, δ, (CDCl$_3$): 1.90 (s,3H); 3.00 (s,3H); 3.32 (s,4H); 4.43 (s,1H); 7.1-7.7 (m,10H)

IR (KBr): 1337, 1165, 941, 703 cm$^{-1}$ i) 3-Amino-1-diphenylmethyl-3-methylazetidine. 14.4 g (43.4 mmol) of 1-diphenylmethyl-3-methyl-3-methylsulphonyloxyazetidine are dissolved in 100 ml of a dioxane solution saturated with ammonia, and the mixture is stirred at 75°-80° C. for 20 hours. It is evaporated to dryness, water is added, the mixture is acidified with acetic acid and extracted with dichloromethane, the organic phase is dried with anhydrous sodium sulphate, the solvent is evaporated off and 8.0 g (73%) of 3-amino-1-diphenylmethyl-3-methylazetidine, melting point 84°-6° C., are obtained.

Spectroscopic data:

$^1$H NMR, δ, (CDCl$_3$): 1.38 (s,3H); 1.73 (s,2H); 2.71 (d,2H,J=8 Hz); 3.10 (d,2H,J=8 Hz); 4.28 (s,1H); 7.0-7.5 (m,10H).

IR (KBr): 3400, 1450, 1247, 626 cm$^{-1}$ 7.75 g (31 mmol) of 3-amino-1-diphenylmethyl-3-methylazetidine are dissolved in 80 ml of methanol and treated with diethyl ether saturated with hydrochloric acid to pH 5-6.

The mixture is evaporated to dryness exhaustively to remove the excess acid and 10.0 g (100%) of 3-amino-1-diphenylmethyl-3-methylazetidine dihydrochloride, melting point 128°-130° C., are obtained.

Spectroscopic data: $^1$H NMR, δ, (DMSO): 1.70 (s,3H); 3.96 (m,2H); 4.36 (m,2H); 6.63 (m,1H); 7.38-7.69 (m,10H); 9.05 (b,3H); 13.17 (b,1H).

IR (KBr): 3400-2300, 1601, 830 cm$^1$

EXAMPLE 2

Preparation of trans-3-amino-1-diphenylmethyl-2-methylazetidine d,e) threo-3-Bromo-1,2-epoxybutane.

Br$_2$ is added dropwise, until the solution assumes a slight coloration (theoretical Br$_2$: 45.4 g, 0.284 mol), to a solution of 20.4 g (0.284 mol) of trans-2-buten-1-ol in 60 ml of chloroform. A few drops of crotyl alcohol are then added until the solution becomes transparent again. The mixture is maintained for 15 minutes at room temperature, the solvent is evaporated off and a dark liquid residue is obtained. This crude 2,3-dibromo-1-butanol is dissolved in 140 ml of ethyl ether, and 16 g (0.284 mol) of potassium hydroxide in 170 ml of water are added to the resulting solution. The mixture is stirred for 2 hours at room temperature, the two layers are separated and the organic layer is washed with water. The solvent is evaporated off, the residue is distilled under vacuum and 24 g (56%) of threo-3-brom-1,2-epoxybutane, boiling point 55°-60° C. at 25 mm Hg, are obtained.

Spectroscopic data:

$^1$H NMR, δ, (CDCl$_3$): 1.68 (d,3H,J=7 Hz); 2.69 (dd,1H,J=5 Hz, J=2.5 Hz); 2.88 (dd,1H,J=5 Hz, J=4 Hz); 3.18 (ddd,1H,J=7 Hz, J=4 Hz, J=2.5 Hz); 3.86 (q,1H, J=7 Hz).

f,g) trans-1-Diphenylmethyl-3-hydroxy-2-methylazetidine.

A solution of threo-3-bromo-1,2-epoxybutane (9.8 g, 64.90 mmol) and aminodiphenylmethane (11.8 g, 64.5 mmol) in 70 ml of methanol is kept stirring for 80 hours at room temperature and 72 hours under reflux. The mixture is evaporated to dryness and the viscous residue is treated with ether and water. The aqueous layer is alkalinized with potassium carbonate and extracted with ethyl ether, and 9.4 g (61%) of trans-1-diphenylmethyl-3-hydroxy-2-methylazetidine are obtained.

Spectroscopic data: $^1$H NMR, δ, (CDCl$_3$): 0.75 (d,J=6 Hz); 2.40 (b,1H); 2.56 (t,1H,J=6 Hz); 3.02 (q,1H,J=6 Hz); 3.64 (t,1H,J=6 Hz); 3.87 (quint.,1H, J=6 Hz); 4.34 (s,1H); 7.27 (m,10H).

IR (film): 3400, 1450, 1156, 749, 702 cm$^{-1}$.

A sample of trans-1-diphenylmethyl-3-hydroxy-2-methylazetidine dissolved in methanol is heated to pH 5-6 with diethyl ether saturated with hydrochloric acid. The mixture is evaporated exhaustively to dryness to remove the excess acid, and trans-1-diphenylmethyl-3-hydroxy-2-methylazetidine hydrochloride, melting point 100°-103° C., is obtained.

h) trans-1-Diphenylmethyl-2-methyl-3-methylsulphonyloxyazetidine.

50 g (0.495 mol) of triethylamine are added to a solution of 77.33 g (0.329 mol) of trans-1-diphenylmethyl-3-hydroxy-2-methylazetidine in 600 ml of dichloromethane and the mixture is cooled to 0° C. The temperature is maintained, a solution of 50 g (0.437 mol) of mesyl chloride is added dropwise and the mixture is left for 24 hours at room temperature. The resulting solution is washed twice with water (300 ml), dried with anhydrous sodium sulphate and evaporated, and an oil is obtained which, when crystallized with petroleum ether, gives 104.6 g (96%) of trans-1-diphenylmethyl-2-methyl-3-methylsulphonyloxyazetidine, melting point 68°-71° C.

$^1$H NMR, δ, (CDCl$_3$): 0.63 (d,3H,J=7 Hz); 2.85 (t,1H,J=6 Hz); 2.96 (s,3H); 3.62 (t,2H,J=6 Hz); 4.39 (s,1H); 4.55 (quint.,1H,J=6 Hz); 7.23 (m,10H).

IR (KBr): 1361, 1339, 1178, 1152, 708 cm$^{-1}$.

i) trans-3-Amino-1-diphenylmethyl-2-methylazetidine.

31 g (93.65 mmol) of trans-1-diphenylmethyl-2-methyl-3-methylsulphonyloxyazetidine are dissolved in a mixture of 150 ml of isopropanol and 100 ml of 30% strength aqueous ammonia solution. The resulting solution is heated to 70° C. for 2-3 hours while the reaction is monitored by thin-layer chromatography.

The mixture is evaporated until the isopropanol has been removed completely (approximately ⅓ of the volume) and the residue is extracted with ethyl ether and water. The aqueous layer is alkalinized and extracted with dichloromethane, and 10 g of the desired diamine are obtained. The ether layer of the first extraction is acidified with dilute (5%) acetic acid, the acidic layer is then alkalinized with sodium hydroxide and extracted with dichloromethane, and 6.3 g of diamine are obtained, making a total obtained of 16.3 g (70%) of trans-3-amino-1-diphenylmethyl-2-methylazetidine, melting point 68°-9° C.

Spectroscopic data:
$^1$H NMR, δ, (CDCl$_3$): 0.64 (d,3H,J=7 Hz); 2.20 (q,1H,J=7 Hz); 2.63 (t,1H,J=7 Hz); 2.90 (quint.,1H,J=7 Hz); 3.50 (t,1H,J=7 Hz); 4.20 (s,1H); 7.20 (m,10H).

IR (KBr): 3270, 1450, 702 cm$^{-1}$ 10.40 g (41.27 mmol) of trans-3-amino-1-diphenylmethyl-2-methylazetidine are dissolved in 100 ml of methanol and treated with ethyl ether saturated with hydrochloric acid to pH 5-6. The mixture is then dried exhaustively to dryness to remove the excess acid, and 13.3 g (100%) of trans-3-amino-1-diphenylmethyl-2-methylazetidine dihydrochloride, melting point 150°-3° C., are obtained.

EXAMPLE 3

Preparation of 1-diphenylmethyl-3-ethylaminomethyl-3-methylazetidine h) 3-Cyano-1-diphenylmethyl-3-methylazetidine.

33.1 g (100 mmol) of 1-diphenylmethyl-3-methyl-3-methylsulphonyloxyazetidine are added to a suspension of sodium cyanide (11 g, 225 mmol) in dimethylformamide (90 ml) and the mixture is stirred at 65°-70° C. for 6 hours. It is cooled and poured onto a water/ice mixture, the product is filtered off, washed with water and dried at 50° C. and 21.75 g (83%) of 3-cyano-1-diphenylmethyl-3-methylazetidine, melting point 86°-88° C., are obtained.

Spectroscopic data:
$^1$H NMR, δ, (CDCl$_3$): 1.60 (s,3H); 3.00 (d,2H,J=7.5 Hz); 3.37 (d,2H,J=7.5 Hz); 4.30 (s,1H); 7.15 (m,10H)

IR (KBr): 2843, 1492, 1452, 745, 706 cm$^{-1}$ i2) 3-Aminomethyl-1-diphenylmethyl-3-methylazetidine.

6.1 g (161 mmol) of lithium aluminium hydride are suspended in 250 ml of tetrahydrofuran, and a solution of 21.1 g (80.5 mmol) of 3-cyano-1-diphenylmethyl-3-methylazetidine in 150 ml of tetrahydrofuran are added dropwise during 1 hour. The temperature is maintained during the addition at between 30° and 35° C. and the mixture is then stirred for 12 hours at room temperature. The excess lithium aluminium hydride is destroyed with ethanol, the insoluble inorganic fraction is filtered off, the tetrahydrofuran is removed, the residue is dissolved with chloroform, the organic phase is washed with water, dried with anhydrous sodium sulphate and evaporated to dryness and 16.1 g (75%) of 3-aminomethyl-1-diphenylmethyl-3-methylazetidine, melting point 46°-8° C., are obtained.

Spectroscopic data:
$^1$H NMR, δ, (CDCl$_3$) 1.1 (s,3H); 1.3 (b,2H); 2.7-3.0 (m,6H); 4.34 (s,1H); 7.2 (m,10H)

IR (KBr): 1452, 744, 704 cm$^{-1}$ i3) 1-Diphenylmethyl-3-methyl-3-trifluoroacetylaminomethylazetidine.

A solution of 14.8 g (69 mmol) of trifluoroacetic anhydride in 50 ml of chloroform are added dropwise to a solution of 14.72 g (55.25 mmol) of 3-aminomethyl-1-diphenylmethyl-3-methylazetidine in 100 ml of chloroform. The temperature is maintained at 20° C. during the addition and the mixture is then stirred for two hours at 25° C. It is washed with water, with 10% strength sodium bicarbonate solution and then again with water, dried with anhydrous sodium sulphate and evaporated, and 16.0 g (80%) of 1-diphenylmethyl-3-methyl-3-trifluoroacetylaminomethylazetidine, melting point 127°-8° C., are obtained.

Spectroscopic data:
$^1$H NMR, δ, (CDCl$_3$): 1.06 (s,3H); 2.85 (d,2H); 3.06 (d,2H); 3.26 (d,2H); 4.30 (s,1H); 7.20 (m,10H); 9.30 (b,1H)

IR (KBr): 2297, 1727, 1175, 1148 cm$^{-1}$.

i4) 1-Diphenylmethyl-3-methyl-3-N-(ethyl)trifluoroacetylaminomethylazetidine 0.16 g (3.6 mmol) of 55% strength sodium hydride is added to a solution of 1.3 g (3.6 mmol) of 1-diphenylmethyl-3-methyl-3-trifluoroacetylaminomethylazetidine in 40 ml of dioxane and 10 ml of dimethylformamide, and the mixture is stirred for two hours at 60°–70° C. The solution is cooled to room temperature, 0.73 g (4.6 mmol) of ethyl iodide is added, the mixture is stirred for 4 hours at 70° C. and evaporated to dryness, the residue is dissolved with chloroform, the organic phase is washed with water, dried with anhydrous sodium sulphate and evaporated and 1.1 g (79%) of 1-diphenylmethyl-3-methyl-3-[N-(ethyl)trifluoroacetylaminomethyl]azetidine are obtained. This compound is dissolved in ethanol, and ethyl ether saturated with hydrochloric acid is added. The product is allowed to crystallize and is filtered off, and 1-diphenylmethyl-3-methyl-3-[N-(ethyl)trifluoroacetylaminomethyl]azetidine hydrochloride, melting point 191°–4° C., is obtained.

Spectroscopic data:

$^1$H NMR, δ, (DMSO-d$_6$): 1.15 (m,3H); 1.36 (s,3H); 3.37 (s,2H); 3.72 (m,3H); 4.0 (m,4H); 6.0 (d,1H); 7.6 (m,10H)

IR (KBr): 1686, 1214, 1149 cm$^{-1}$.

i5) 1-Diphenylmethyl-3-ethylaminomethyl-3-methylazetidine 3.9 g (10 mmol) of 1-diphenylmethyl-3-methyl-3-[N-(ethyl)trifluoroacetylaminomethyl]azetidine in 20 ml of 5% strength sodium hydroxide and 20 ml of ethanol are stirred for one hour at 70° C. The solution is cooled, brought to pH 8 with hydrochloric acid, acidified with acetic acid and evaporated, the residue is extracted with chloroform, the organic phase is dried with anhydrous sodium sulphate, the solvent is evaporated off and 2.5 g (85%) of 1-diphenylmethyl-3-ethylaminomethyl-3-methylazetidine are obtained.

Spectroscopic data: $^1$H NMR, δ, (CDCl$_3$): 1.05 (t,3H); 1.20 (s,3H); 2,4–3.1 (m,9H); 4.31 (s,1H); 7.0–7.6 (m,10H)

IR (film): 2962, 2922, 1452, 753, 743, 703 cm$^{-1}$.

The synthesis of Examples 4 to 17 is performed by following the method of the above examples. The melting point and the infrared spectroscopic data of Examples 1 to 17 are presented in Table 1, and the corresponding proton nuclear magnetic resonance values are presented in Table 2.

According to a protocol similar to that described above, the following derivatives also are obtained by way of compounds according to the invention:
cis-3-amino-1-diphenylmethyl-2-ethylazetidine;
3-amino-2,2-dimethyl-1-diphenylmethylazetidine;
(2R,3R)-3-amino-1-diphenylmethyl-2-methylazetidine;
(2S,3S)-3-amino-1-diphenylmethyl-2-methylazetidine;
(2R,3S)-3-amino-1-diphenylmethyl-2-methylazetidine;
(2S,3R)-3-amino-1-diphenylmethyl-2-methylazetidine.

TABLE 1

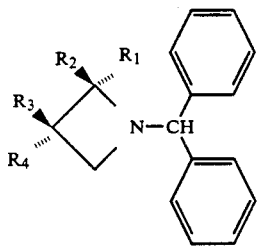

| Example | R$_1$ | R$_2$ | R$_3$ | R$_4$ | Isomer | Base Salt | M.p. (°C.) | IR (KBr), cm$^{-1}$ | [α]$_D$ c = 0.3 (CHCl$_3$) Base |
|---|---|---|---|---|---|---|---|---|---|
| 1 | H | H | —NH$_2$ | CH$_3$ | — | Base | 84–86 | 3400, 1450, 1247, 626 | — |
| 1 | H | H | —NH$_2$ | CH$_3$ | — | 2HCl | 128–130 | 3400–2300, 1601, 830 | — |
| 2 | CH$_3$ | H | —NH$_2$ | H | trans | Base | 68–69 | 3270, 1450, 702 | — |
| 2 | CH$_3$ | H | —NH$_2$ | H | trans | 2HCl | 150–153 | 3400–2300, 1453, 704 | — |
| 3 | H | H | —CH$_2$NHCH$_2$CH$_3$ | CH$_3$ | — | Base | (Oil) | 2962, 2922, 1452, 753, 743, 703 | — |
| 4 | H | H | —CH$_2$N(Et)COCF$_3$ | CH$_3$ | — | HCl | 191–194 | 1686, 1214, 1149 | — |
| 5 | H | H | —CH$_2$NHCOCF$_3$ | CH$_3$ | — | Base | 127–128 | 2297, 1727, 1175, 1148 | — |
| 6 | H | H | —CH$_2$NH$_2$ | CH$_3$ | — | Base | 46–48 | 1452, 744, 704 | — |
| 7 | H | H | —NHCH$_3$ | CH$_3$ | — | Base | 62–63 | 3293, 2820, 1450, 705 | — |
| 8 | H | H | —N(CH$_3$)$_2$ | CH$_3$ | — | Base | 53–54 | 2824, 1235, 706 | — |
| 8 | H | H | —N(CH$_3$)$_2$ | CH$_3$ | — | 2HCl | 190–192 | 2361, 1453, 1422, 756, 706 | — |
| 9 | CH$_3$ | H | —NHCH$_3$ | H | trans | Base | 93–95 | 1960, 2920, 1470, 705 | — |
| 10 | CH$_3$ | H | —N(CH$_3$)$_2$ | H | trans | 2HCl | 149–152 | 3600–3100, 1457, 752, 706 | — |
| 11 | CH$_3$ | H | —CH$_2$NH$_2$ | H | trans | Base | 84–87 | 3402, 2870, 1453, 704 | — |
| 12 | CH$_3$ | H | —CH$_2$NHCOCF$_3$ | H | trans | Base | 122–125 | 3292, 1705, 1180, 703 | — |
| 13 | CH$_3$ | H | —CH$_2$N(Et)COCF$_3$ | H | trans | HCl | 95–101 | 1689, 1456, 1187, 705 | — |
| 14 | H | CH$_3$ | —NH$_2$ | H | cis | 2HCl | 135–138 | 3350, 1492, 1451, 704 | — |
| 15 | CH$_3$ | H | —NH$_2$ | CH$_3$ | r-3-amino--trans-2- | 2HCl | 172–174 | 3500–2200, 1457, 1390, 753, 704 | — |
| 16 | H | H | —NHCOCF$_3$ | CH$_3$ | — | HCl | (Oil) | 3300, 1784, 1700, 1162, 704 (film) | — |
| 17 | H | H | —CH$_2$NHCOCH$_3$ | CH$_3$ | — | Base | (Oil) | 3300, 1656, 1556, 788, 704 (film) | — |
| 18 | H | CH$_3$CH$_2$ | —NH$_2$ | H | cis | Base | B.p. 200–235 (0.65 torr) | 3380, 3312, 1600, 1492, 1451, (film) | — |
| 18 | H | CH$_3$CH$_2$ | —NH$_2$ | H | cis | 2HCl | 123–125 | 3412, 2931, 1450, 750, 700 | — |
| 19 | CH$_3$ | CH$_3$ | —NH$_2$ | H | — | Base | 103–106 | 3368, 3000, 1587, 1493, 1450 | — |
| 19 | CH$_3$ | CH$_3$ | —NH$_2$ | H | — | 2HCl | 150–152 | 3412, 2943, 1450, 1122, 743, 700 | — |
| 20 | H | CH$_3$ | —NH$_2$ | H | 2R, 3R | 2HCl | 128–130 | 3348, 1492, 1450, 703 | +74.0 |
| 21 | CH$_3$ | H | H | —NH$_2$ | 2S, 3S | 2HCl | 130–132 | 3348, 1492, 1450, 703 | −73.3 |

TABLE 1-continued

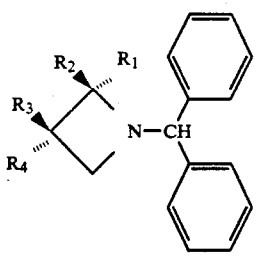

| Example | R₁ | R₂ | R₃ | R₄ | Isomer | Base Salt | M.p. (°C.) | IR (KBr), cm⁻¹ | [α]$_D$ c = 0.3 (CHCl₃) Base |
|---|---|---|---|---|---|---|---|---|---|
| 22 | H | CH₃ | H | —NH₂ | 2R, 3S | 2HCl | 151–153 | 3400–2300, 1453, 704 | +112.3 |
| 23 | CH₃ | H | —NH₂ | H | 2S, 3R | 2HCl | 152–153 | 3400–2300, 1453, 704 | −110.3 |

TABLE 2

| Example | ¹HNMR, δ, (CDCl₃) or (DMSO-D₆)* |
|---|---|
| 1 | 1.38 (s, 3H); 1.73 (s, 2H); 2.71 (d, 2H, J=8 Hz); 3.10 (d, 2H, J=8 Hz); 4.28 (s, 1H); 7.0–7.5 (m, 10H) |
| 1.2 HCl | *1.70 (S, 3H); 3.96 (m, 2H); 6.63 (m, 1H); 7.38–7.69 (m, 10H); 9.05 (b, 3H); 13.17 (b, 1H) |
| 2 | 0.64 (d, 3H, J=7Hz); 2.20 (q, 1H, J=7z); 2.63 (t, 1H, J=7Hz) 2.90 (quint., 1H, J=7Hz); 3.50 (t, 1, J=7Hz); 4.20 (s, 1H); 7.20 (m, 10H) |
| 3 | 1.05 (t, 3H); 1.20 (s, 3H); 2.4–3.1 (m, 9H); 4.31 (s, 1H); 7.0–7.6 (m, 10H) |
| 4.HCl | *1.15 (m, 3H); 1.36 (s, 3H); 3.37 (s, 2H); 3.72 (m, 3H), 4.0 (m, 4H); 6.0 (d, 1H); 7.6 (m, 10) |
| 5 | 1.06 (s, 3H); 2.85 (d, 2H); 3.06 (d, 2H); 3.26 (d, 2H); 4.30 (s, 1H); 7.20 (m, 10H); 9.3 (b, 1H) |
| 6 | 1.1 (s, 3H); 1.30 (b, 2H); 2.7–3.0 (m, 6H); 4.34 (s, 1H); 7.2 (m, 10H) |
| 7 | 1.3 (s, 1H); 1.4 (s, 3H); 2.2 (s, 3H); 2.60 (d, 2H); 3.0 (d, 2H); 4.2 (s, 1H); 7.25 (m, 10H) |
| 8 | 1.28 (s, 3H); 2.07 (s, 6H); 2.88 (d, 2H, J=7Hz); 3.05 (d, 2H, J=7Hz); 4.43 (s, 1H); 7.30 (m, 10H) |
| 9 | 0.8 (d, 3H, J=6Hz); 1.2 (b, 1H); 2.28 (s, 3H); 2.29 (m, 1H); 2.85 (m, 2H); 3.5 (m, 1H); 4.25 (s, 1H); 7.25 (m, 10H) |
| 10 | 0.75 (d, 3H, J=6Hz); 2.05 (s, 6H); 2.35 (q. 1H, J=6, 5Hz); 2.6 (t, 1H, J=6, 5Hz); 3.15 (quint., 1H, J=6, 5Hz); 3.5 (t, 1H, J=6, 5Hz); 4.4 (s. 1H); 7.3 (m, 10H) |
| 11 | 0.75 (d, 3H); 1.36 (b, 2H); 2.10 (sext., 1H); 2.42 (t, 1H); 2.71 (d, 2H); 2.97 (quint., 1H); 3.45 (t, 1H); 4.3 (s, 1H); 7.3 (m, 10H) |
| 12 | 0.85 (d, 3H); 2.25 (sext., 1H); 2.55 (t, 1H); 3.16 (quint., 1H); 3.50 (m, 3H); 4.41 (s, 1H); 6.98 (b, 1H); 7.33 (m, 10H) |
| 13.HCl | 1.0 (m, 5H); 2.8 (m, 1H); 3.2 (q, 2H); 3.6 (d, 2H); 3.95 (m, 1H); 4.5 (m, 1H); 5.65 (d, 1H); 7.21–7.75 (m, 10H); 12.17 (b, 1H) |
| 14 | 0.63 (d, 3H, J=6Hz); 1.64 (b, 2H); 3.09 (m, 2H); 3.35 (m, 2H); 4.34 (s, 1H); 7.27 (m, 10H) |
| 15 | 0.53 (d, 3H, J=6, 5Hz); 1.26 (s, 3H); 1.51 (b, 2H); 2.41 (d, 1H, J=7Hz); 2.84 (q, 1H, J=7Hz); 3.25 (d, 1H, J=7Hz); 4.27 (s, 1H); 7.26 (m, 10H) |
| 16 | 1.56 (s, 3H); 3.18 (s, 4H); 4.38 (s, 1H); 7.25 (m, 10H); 9.2 (b, 1H) |
| 17 | 1.05 (s, 3H); 1.91 (s, 3H); 2.70 (d, 2H, J=7, 6Hz); 2.96 (d, 2H, J=7, 6Hz, 3.20 (d, 2H, J=5Hz); 4.24 (s, 1H); 6.25 (m, 10H); 9.2 (b, 1H) |
| 18 | 0.54 (m, 3H); 1.45 (m, 2H); 1.71 (b, 2H); 3.04 (m, 3H); 3.46 (dt, J=6, 2Hz, J'=2, 3Hz, 1H); 4.29 (s, 3H); 7.05–7.42 (m, 10H) |
| 19 | 1.00 (s, 6H); 1.51 (b, 2H); 2.51 (t, J=6, 1Hz, 1H); 3.26 (m, 2H); 4.54 (s, 1H); 7.10–7.55 (m, 10H) |
| 20 | 0.63 (d, 3H, J=6Hz); 1.64 (s, 2H); 3.09 (m, 2H); 3.35 (m, 2H); 4.34 (s, 1H); 7.27 (m, 10H) |
| 21 | 0.63 (d, 3H, J=6Hz); 1.64 (s, 2H); 3.09 (m, 2H); 3.35 (m, 2H); 4.34 (s, 1H); 7.27 (m, 10H) |
| 22 | 0.64 (d, 3H, J=7Hz); 2.20 (q, 1H, J=7Hz); 2.63 (t, 1H, J=7Hz); 2.90 (quint., 1H, J=7Hz); 3.50 (t, 1H, J=7Hz); 4.20 (s, 1H); 7.20 (m, 10H) |
| 23 | 0.64 (d, 3H, J=7Hz); 2.20 (q, 1H, J=7Hz); 2.63 (t, 1H, J=7Hz); 2.90 (quint., 1H, J=7Hz); 3.50 (t, 1H, J=7Hz); 4.20 (s, 1H); 7.20 (m, 10H) |

EXAMPLE 1 A

Preparation of 3-amino-3-methylazetidine dihydrochloride 10 g (31 mmol) of 3-amino-1-diphenylmethyl-3-methylazetidine dihydrochloride are dissolved in 120 ml of methanol, and 2 g of Pd(OH):, i.e. 20% by weight, are added. The mixture is maintained for 12 hours with hydrogen under pressure (15 atm.), the catalyst is filtered off, the solvent is evaporated off, the diphenylamine originating from the reaction is removed and the product is washed with benzene and carbon tetrachloride. The resulting residue is recrystallized with methanol, and 3.85 g (78%) of 3-amino-3-methylazetidine dihydrochloride, melting point 196°–9° C., are obtained.

Spectroscopic data:

¹H NMR, δ, (DMSO-d₆): 1.66 (s,3H); 3.81 (d,2H,J=10.5 Hz); 4.31 (d,2H,J=10.5 Hz); 9.32 (b,5H).

IR (KBr): 3300–2300, 1575, 1515, 1232 cm⁻¹.

The synthesis of Examples 2A to 16A is performed by following the method of Example 1A. The corresponding melting point, infrared spectroscopic and proton nuclear magnetic resonance results are presented in Tables 3 and 4.

TABLE 3

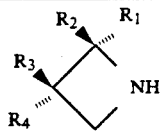

| Example | R₁ | R₂ | R₃ | R₄ | Isomer | Base Salt | M.p. (°C.) | IR (KBr), cm⁻¹ |
|---|---|---|---|---|---|---|---|---|
| 1A | H | H | —NH₂ | CH₃ | — | 2HCl | 196–199 | 3300–2300, 1575, 1515, 1232 |
| 2A | CH₃ | H | —NH₂ | H | trans | 2HCl | 165–168 | 3500–2100, 1561, 1451, 1365, 1043 |
| 4A | H | H | —CH₂N(Et)COCF₃ | CH₃ | — | HCl | 120–123 | 2960, 1688, 1270, 1190, 1130 |
| 5A | H | H | —CH₂NHCOCF₃ | CH₃ | — | HCl | 187–192 | 3327, 2939, 1729, 1209, 1186, 1157 |
| 6A | H | H | —CH₂NH₂ | CH₃ | — | 2HCl | 223–226 | 2980, 2940, 1580, 1500 |
| 8A | H | H | —N(CH₃)₂ | CH₃ | — | 2HCl | 185–186 | 3120, 2870, 1458, 1190 |
| 9A | CH₃ | H | —NHCH₃ | H | trans | 2HCl | (Oil) | 2925, 1618, 1450, 1075 |
| 10A | CH₃ | H | —N(CH₃)₂ | H | trans | 2HCl | 170–174 | 3300–2300, 1473, 1382, 1252 |
| 12A | CH₃ | H | —CH₂NHCOCF₃ | H | trans | HCl | 130–132 | 3068, 1728, 1215, 1157 |
| 13A | CH₃ | H | —CH₂N(Et)COCF₃ | H | trans | HCl | 180–182 | 2900, 1685, 1222, 1106 |
| 14A | H | CH₃ | —NH₂ | H | cis | 2HCl | 181–183 | 3300–2200, 1561, 1338, 1188, 1051 |
| 15A | CH₃ | H | —NH₂ | CH₃ | 3-r-amino-2-trans | 2HCl | 180–183 | 3300–2300, 1596, 1554, 1159 |
| 16A | H | H | —NHCOCF₃ | CH₃ | — | HCl | (Oil) | 3600–2500, 1713, 1555, 1450, 1187 |
| 17A | CH₃ | H | —N(CH₃)COCF₃ | H | trans | HCl | 133–134 | 2900, 1715, 1270, 1215, 1110 |
| 17B | H | H | —N(CH₃)COCF₃ | CH₃ | — | HCl | 175–179 | 3480, 2900, 1686, 1153 |
| 18A | H | CH₃CH₂ | —NH₂ | H | cis | 2HCl | (Oil) | 3600–2500, 1600, 1462, 1325 |
| 19A | CH₃ | CH₃ | —NH₂ | H | — | 2HCl | 168–171 | 3431, 2968, 1581, 1543, 1512 |
| 20A | H | CH₃ | —NH₂ | H | 2R,3R | 2HCl | 180–184 | 3300–2200, 1561, 1340 |
| 21A | CH₃ | H | H | —NH₂ | 2S,3S | 2HCl | 181–186 | 3295–2200, 1561, 1340 |
| 22A | H | CH₃ | H | —NH₂ | 2R,3S | 2HCl | 164–166 | 3500–2100, 1561, 1451, 1365, 1043 |
| 23A | CH₃ | H | —NH₂ | H | 2S,3R | 2HCl | 163–165 | 3500–2100, 1561, 1451, 1365, 1043 |

TABLE 4

| Example | ¹HNMR, δ, (DMSO-D₆) |
|---|---|
| 1A | 1.66 (s, 3H); 3.81 (d, 2H, J=10, 5Hz); 4.31 (d, 2H, J=10, sHz); 9.32 (b, 5H) |
| 2A | 1.51 (d, 3H, J=7Hz); 3.92 (m, 3H); 4.60 (m, 1H); 9.20 (b, 5H) |
| 4A | 1.15 (t, 3H); 1.25 (s, 3H); 3.4 (q, 2H); 3.57 (s, 2H); 3.6 (d, 2H, J=9Hz); 3.92 (d, 2H, J=9Hz); 9.60 (b, 2H) |
| 5A | 1.24 (s, 3H); 3.38 (s, 2H); 3.54 (m, 2H); 3.83 (m, 2H); 9.39 (b, 1H); 9.78 (b, 2H) |
| 6A | 1.35 (s, 3H); 3.13 (s, 2H); 3.58 (d, 2H, J=11Hz); 3.91 (d, 2H, J=11Hz); 8.77 (b, 5H) |
| 8A | 1.58 (s, 3H); 2.50 (s, 6H); 3.65 (d, 2H, J=8Hz); 4.34 (d, 2H, J=8Hz); 9.95 (b, 3H) |
| 9A | 1.6 (d, 3H): 2.6 (s, 3H); 3.5 (m, 1H); 4.0 (m, 2H); 4.8 (m, 1H); 9.7 (b, 2H); 10.2 (b, 2H) |
| 10A | 1.51 (d, 3H); 2.70 (s, 6H); 4.04 (m, 3H); 4.60 (m, 1H); 9.95 (b, 3H) |
| 12A | 1.00 (d, 3H); 3.30 (m, 6H); 9.40 (m, 3H) |
| 13A | 1.12 (t, 3H); 1.15 (d, 3H); 3.41 (m, 8H); 9.9 (b, 1H); 10.1 (b, 1H) |
| 14A | 1.59 (d, 3H); 4.09 (m, 3H); 4.59 (m, 1H); 9.21 (b, 5H) |
| 15A | 1.38 (d, 3H); 1.53 (s, 3H); 3.57 (d, 1H, J=9, 5Hz); 4.13 (d, 1H, J=9, 5Hz); 4.67 (m, 1H); 9.21 (b, 5H) |
| 16A | 1.47 (s, 3H); 3.70 (m, 4H); 9.45 (b, 3H) |
| 17A | 1.48 (d, 3H); 3.42 (s, 3H); 4.0 (m, 2H); 4.65 (m, 2H); 9.51 (b, 2H) |
| 17B | 1.60 (s, 3H); 2.96 (s, 3H); 3.70 (d, 2H, J=11Hz); 4.19 (d, 2H, J=11Hz); 9.56 (b, 2H) |
| 18A | 0.92 (b, 3H); 2.07 (m, 2H); 3.42 (m, 1H); 4.15 (m, 3H); 9.26 (m, 5H) |
| 19A | 1.59 (s, 3H); 1.68 (s, 3H); 3.80–4.20 (m, 3H); 9.16 (m, 5H) |
| 20A | 1.59 (d, 3H); 4.09 (m, 3H); 4.59 (m, 1H); 9.21 (b, 5H) |
| 21A | 1.59 (d, 3H); 4.09 (m, 3H); 4.59 (m, 1H); 9.21 (b, 5H) |
| 22A | 1.51 (d, 3H, J=7Hz); 3.92 (m, 3H); 4.60 (m, 1H); 9.20 (b, 5H) |
| 23A | 1.51 (d, 3H, J=7Hz); 3.92 (m, 3H); 4.60 (m, 1H); 9.20 (b, 5H) |

We claim:

1. New azetidines, having the formula (I)

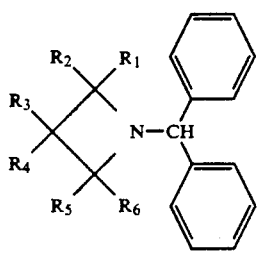

(I)

in which

R₃ represents a radical having up to five carbon atoms selected from the group consisting of an amino radical, an alkylamino radical, a dialkylamino radical, a cycloalkylamino radical, an acylamino radical, an alkylacylamino radical, an aminomethyl radical, an alkylaminomethyl radical, an acylaminomethyl radical or an alkylacylaminomethyl radical, in which radicals each acyl fragment may be substituted with one or more halogen atoms; and R₁, R₂, R₄, R₅ and R₆ represent a hydrogen atom or a lower alkyl radical, with the proviso that at least one of them represents a lower alkyl radical, or their physiologically acceptable salts.

2. Azetidines in accordance with claim 1 in which halogen substituent on an acyl fragment is a fluorine atom.

3. The compounds corresponding to the general formula (I) according to claim 1, selected from the following group:

3-amino-1-diphenylmethyl-3-methylazetidine;
trans-3-amino-1-diphenylmethyl-2-methylazetidine;
1-diphenylmethyl-3-ethylaminomethyl-3-methylazetidine;
1-diphenylmethyl-3[N-(ethyl)trifluoroacetylaminomethyl]-3-methylazetidine;
1-diphenylmethyl-3-methyl-3-trifluoroacetylaminomethylazetidine;
3-aminomethyl-1-diphenylmethyl-3-methylazetidine;
1-diphenylmethyl-3-methyl-3-methylaminoazetidine;
3-dimethylamino-1-diphenylmethyl-3-methylazetidine;
trans-1-diphenylmethyl-2-methyl-3-methylaminoazetidine;
trans-3-dimethylamino-1-diphenylmethyl-2-methylazetidine;
trans-3-aminomethyl-1-diphenylmethyl-2-methylazetidine;
trans-1-diphenylmethyl-2-methyl-3-trifluoroacetylaminomethylazetidine;
trans-1-diphenylmethyl-3-[N-(ethyl)trifluoroacetylaminomethyl]-2-methylazetidine;
cis-3-amino-1-diphenylmethyl-2-methylazetidine;
r-3-amino-3,trans-2-dimethyl-1-diphenylmethylazetidine;
1-diphenylmethyl-3-methyl-3-trifluoroacetylaminoazetidine;
3-acetylaminomethyl-1-diphenylmethyl-3-methylazetidine;
cis-3-amino-1-diphenylmethyl-2-ethylazetidine;
3-amino-2,2-dimethyl-1-diphenylmethylazetidine;
(2R,3R)-3-amino-1-diphenylmethyl-2-methylazetidine;
(2S,3S)-3-amino-1-diphenylmethyl-2-methylazetidine;
(2R,3S)-3-amino-1-diphenylmethyl-2-methylazetidine;
(2S,3R)-3-amino-1-diphenylmethyl-2-methylazetidine.

* * * * *